US012708640B2

(12) United States Patent
Samant et al.

(10) Patent No.: US 12,708,640 B2
(45) Date of Patent: Aug. 18, 2026

(54) SYNERGISTIC NUTRITIONAL COMPOSITIONS FOR TREATING VESTIBULAR ASSOCIATED NEURODEGENERATIVE DISEASES

(71) Applicants: CELAGENEX RESEARCH (INDIA) PVT. LTD., Thane (IN); Manoj Tongra, Jaipur (IN)

(72) Inventors: Rajaram Samant, Thane West (IN); Rajendra Prasad Tongra, Jaipur (IN)

(73) Assignee: CELAGENEX RESEARCH (INDIA) PVT. LTD. (IN)

( * ) Notice: Subject to any disclaimer, the term of this patent is extended or adjusted under 35 U.S.C. 154(b) by 466 days.

(21) Appl. No.: 18/273,749

(22) PCT Filed: Jan. 21, 2022

(86) PCT No.: PCT/IN2022/050048
§ 371 (c)(1),
(2) Date: Jul. 21, 2023

(87) PCT Pub. No.: WO2022/157808
PCT Pub. Date: Jul. 28, 2022

(65) Prior Publication Data

US 2024/0100077 A1 Mar. 28, 2024

(30) Foreign Application Priority Data

Jan. 23, 2021 (IN) ............................ 202021046380

(51) Int. Cl.
*A61K 31/7072* (2006.01)
*A61K 31/198* (2006.01)
*A61P 25/00* (2006.01)

(52) U.S. Cl.
CPC ........ *A61K 31/7072* (2013.01); *A61K 31/198* (2013.01); *A61P 25/00* (2018.01)

(58) Field of Classification Search
CPC .... A61K 31/7072; A61K 31/198; A61P 25/00
See application file for complete search history.

(56) References Cited

U.S. PATENT DOCUMENTS

| | | | | |
|---|---|---|---|---|
| 3,991,077 | A * | 11/1976 | Uzuki ..................... | C12P 13/04 548/338.1 |
| 4,960,759 | A | 10/1990 | De Luca et al. | |
| 8,518,882 | B2 | 8/2013 | Wurtman et al. | |
| 2019/0083438 | A1 | 3/2019 | Factor et al. | |

FOREIGN PATENT DOCUMENTS

| | | | | |
|---|---|---|---|---|
| CN | 111961102 | A * | 11/2020 | ............ C07H 19/10 |
| EP | 2 575 793 | B1 | 6/2018 | |
| EP | 3 583 940 | A1 | 12/2019 | |
| IN | 20192101574 | A * | 11/2021 | |
| WO | 2005/112635 | A2 | 12/2005 | |
| WO | 2011/151685 | A1 | 12/2011 | |
| WO | 2013/049686 | A1 | 4/2013 | |
| WO | 2018/229738 | A1 | 12/2018 | |
| WO | 2020/178721 | A1 | 9/2020 | |

OTHER PUBLICATIONS

Niazi, S.K., Handbook of Pharmaceutical Manufacturing Formulations, vol. 1, 2009, Informa Healthcare USA, Inc., p. 99-169. (Year: 2009).*

Ferber-Viart, C., et al., "Effects of Acetyl-DL-Leucine in Vestibular Patients: A Clinical Study following Neurotomy and Labyrinthectomy," Audiol Neurotol, vol. 14, Issue 1, pp. 17-25 (Jul. 29, 2008).

* cited by examiner

*Primary Examiner* — Jonathan S Lau

(57) ABSTRACT

The invention disclosed herein relates to synergistic nutritional compositions for treating vestibular associated neurodegenerative diseases. Particularly, the invention relates to synergistic nutritional compositions comprising an exogenous blend of N-acetyl-DL-leucine (NADLL) enantiomerically enriched with L-leucine and uridine monophosphate (UMP) which are present in a weight ratio of 1:0.002 to 1:0.8 along with pharmaceutically acceptable excipients. The composition of the present invention is useful for treating dizziness, imbalance, vertigo, tinnitus, hearing loss, brain fog, vision impairment, cognitive changes, Alzheimer's disease, progressive supranuclear palsy (PSP), frontotemporal dementia (FTD), motor neurone disease (MND), multiple system atrophy (MSA), and Parkinson's disease (PD).

7 Claims, 3 Drawing Sheets

% of Rats that successfully righted themselves within 5sec
100
90
80
70
60
50
40
30
20
10
0
G1
G2
G3
G4
G5
G6
G7
Groups Recovery time for position correction (in Sec)
45
40
35
30
25
20
15
10
5
0
G1
G2
G3
G4
G5
G6
G7
Groups 300
250
200
150
100
50
0
Ambulation Score
G1
G2
G3
G4
G5
G6
G7
Groups 12
10
8
6
4
2
0
Rearing Responses
G1
G2
G3
G4
G5
G6
G7
Groups Defecation
5
4.5
4
3.5
3
2.5
2
1.5
1
0.5
0
G1
G2
G3
G4
G5
G6
G7
Groups Grooming Score
9
8
7
6
5
4
3
2
1
0
G1
G2
G3
G4
G5
G6
G7
Groups

SYNERGISTIC NUTRITIONAL COMPOSITIONS FOR TREATING VESTIBULAR ASSOCIATED NEURODEGENERATIVE DISEASES

FIELD OF THE INVENTION

The present invention relates to synergistic nutritional compositions for treating vestibular related neurodegenerative diseases. Particularly, the invention relates to synergistic nutritional compositions comprising an exogenous blend or combination of N-acetyl-DL-leucine (NADLL), enantiomerically enriched with L-leucine, and uridine monophosphate (UMP) which are present in a specific weight ratio. The composition of the present invention is useful for treating dizziness, imbalance, vertigo, tinnitus, hearing loss, brain fog, vision impairment, cognitive changes, Alzheimer's disease, progressive supranuclear palsy (PSP), frontotemporal dementia (FTD), motor neurone disease (MND), multiple system atrophy (MSA), and Parkinson's disease (PD).

BACKGROUND OF THE INVENTION

The vestibular system includes parts of the inner ear and brain that help control balance and eye movements. In a normal functioning vestibular system, when the head is still, the discharge at the level of the vestibular nuclei is equal; therefore, the eyes are still when the head is still. Again, in a normal functioning vestibular system, when the head moves, the activity at the level of the vestibular nuclei changes. The right and left vestibular nuclei communicate with each other through commissural connections. If the system is damaged by disease, ageing, or injury, vestibular disorders can result, and are often associated with one or more of these symptoms, like dizziness, imbalance, vertigo, tinnitus, hearing loss, brain fog, vision impairment, cognitive changes, benign paroxysmal positional vertigo (BPPV), vestibular migraine, labyrinthitis or vestibular neuritis, Ménière's disease, age-related dizziness and imbalance, vestibular damage due to head injury, secondary endolymphatic hydrops, perilymph fistula and like thereof.

Vestibular disorder is a sensation of feeling off-balance. It is a false feeling of spinning or that the world around us is spinning. Dizziness is also describing various sensations of light headedness, imbalance, and illusory feelings of movement or disorientation. Vestibular disorder is often caused by an inner ear problem. Vertigo is a specific subtype of dizziness which originates in the inner ear labyrinth. The most common cause of vertigo is BPPV (benign paroxysmal positional vertigo). BPPV occurs when tiny calcium particles (canaliths) clump up in canals of the inner ear. The calcium deposits in the inner ear become dislodged from the otolithic membrane and settle in the semi-circular canals. Any change in the position of the head causes these tiny crystals to shift, thereby triggering dizziness.

About 50% of all vertigo in older people is due to BPPV. The inner ear sends signals to the brain about head and body movements relative to gravity. It helps to keep body balance. One of the epidemiological studies estimates that, as many as 35% adults aged 40 years or older in the United States, which is approximately 69 million Americans, have experienced some form of vestibular dysfunction. According to the National Institute on Deafness and Other Communication Disorders (NIDCD), a further 4% (8 million) of American adults report a chronic problem with balance, while an additional 1.1% (2.4 million) of American adults reports a chronic problem with dizziness alone. Also, 80% of people aged 65 years and older have experienced dizziness. BPPV has been the most common vestibular disorder and is the cause of approximately 50% of dizziness in older people.

Generally, vestibular suppressant and antiemetic drugs are the main treatment of vertigo. Vestibular suppressants include three general drug classes: anticholinergics, antihistamines, and benzodiazepines. Examples of antihistamine-anticholinergics are meclizine and dimenhydrinate and benzodiazepines are lorazepam and diazepam. It is observed that antihistamines are potent muscarinic receptor antagonists that can lead to serious anticholinergic side effects, such as sinus tachycardia, dry skin, dry mucous membranes, dilated pupils, constipation, ileus, urinary retention, and agitated delirium.

During the chronic phase of vestibular system dysfunction, symptoms must be actively experienced without interference in order for the brain to adjust, a process called vestibular compensation. Vestibular compensation is often referred to as central compensation. In the world of vestibular function, central generally refers to brain function, while peripheral generally refers to ear function. Central compensation refers to the process by which the brain adapts to stable changes in inner ear function, gets rid of imbalance in tone, and readjusts gain.

Since vestibular suppressants can slow down or stop the process of central compensation, they are often not appropriate for long-term use. Physicians generally find that most patients who fail to compensate are either strictly avoiding certain movements, using vestibular suppressants daily, or both. Hence a need arises to find out nutrient based vestibular suppressants with no severe side effects.

N-acetyl-DL-leucine is well known for the treatment of vestibular dysfunctions. Since 1957, acetyl-dl-leucine, an acetylated derivative of a natural amino acid, has been widely used for the symptomatic treatment of acute vertigo and dizziness and to improve central vestibular compensation. There are some prior arts which disclose about acetyl-leucine and its medicinal use.

US20190083438A1 is directed to use of acetyl-leucine for improving cognitive function, mobility, or cognitive function and mobility in elderly patients aged 70 and over. Similarly, EP3583940A1 relates to use of acetyl-leucine in treating neurodegenerative diseases associated with lysosomal dysfunction.

Further, WO2020/178721A1 provides methods of treating traumatic brain injury, in a patient in need thereof by administering a therapeutically effective amount of acetyl-dl-leucine. Also, WO2018229738A1 relates to leucine, acetyl-leucine, and their use in the treatment of migraine.

EP2575793B1 relates to the use of N-acetyl-DL-leucine for the prevention and/or treatment of eye diseases or disorders or ophthalmologic diseases inducing a decrease of visual function and/or age-related physiological vision decline.

It is interestingly found that vestibular disorders not only affect adults, but also children. Nowadays, paediatric vestibular disorders are receiving increasing attention from clinicians as an overlooked problem. In addition to impairments of motor development and balance, vestibular deficits may cause poor gaze stability that inhibits children from learning to read. [Jeremy Hinton-2018, Vestibular.org: 077/Anatomy]

Notably, for more than a decade, evidence from animal studies has suggested that damage to the vestibular system leads to deficits in spatial navigation which are indicative of impaired spatial learning and memory. There are evidence and clinical studies which reveal that humans with vestibular disorders exhibit a range of cognitive deficits. Moreover, humans with vestibular disorders are likely to experience cognitive dysfunction which is not necessarily related to any particular episode of vertigo or dizziness, and therefore may occur even in patients who are otherwise well compensated.

Previous studies have reported an association between vestibular dysfunction and various forms of cognitive impairments, including visuospatial ability, attention, executive function, and memory. Although the mechanism of the association between vestibular dysfunction and cognitive impairments is still unclear, several potential pathways have been hypothesized. For example, vestibular dysfunction may contribute to atrophy of areas of the cortical vestibular network, including the hippocampus, which may in turn be responsible for the deterioration of memory and visuospatial ability. [N. Sugaya et al., *Scientific Reports* 8, Article number 9984 (2018)]

Additionally, the high prevalence of affective disorders in individuals with vestibular impairment may also contribute to cognitive dysfunction. Thus, both improvements in dizziness and emotional distress by vestibular recovery may contribute to changes in cognitive function in patients with intractable dizziness.

Remarkably, Johns Hopkins University School of Medicine Researchers have reported that vestibular function is an important mediator of the association between age and lower cognitive performance. They also suggested that vestibular impairment contributes to worse cognitive outcomes, which in turn may result in critical adverse geriatric outcomes including falls and activities of daily living (ADL) difficulty. Future studies will need to establish whether mitigating age-related decline in vestibular sensitivity will forestall these highly morbid and costly outcomes. [*Journal of Gerontology: Med. Sci.,* 2016, 71, 2]

These findings may also be related to the observation that patients with vestibular deficits experience a high incidence of depression and anxiety disorders. [Paul F. Smith et al. 2004 *Journal of Vestibular Research* 15 (2005) 1-9)]

One of the first clinical studies of cognitive function following vestibular loss was reported by Grimm et al. [*Acta Otolaryngol. Suppl.* 464, 1-40; 1989]. This study describes those patients with symptoms such as positional vertigo as also having a variety of psychological symptoms, including memory and attention deficits. Out of a total of 102 patients, more than 85% of them reported memory loss. Their performance on digit symbol, block design, paired associate learning and picture arrangement tasks, was impaired. Further, studies in the 1990's examined the effects of vestibular damage on spatial navigation in humans and demonstrated that patients with vestibular disorders exhibited deficits in path navigation. [Paul F. Smith et al. *Front Integr Neurosci.* 2013; 7: 84]

However, the inventors of the present invention have found that N-acetyl-DL-leucine is not working efficiently in the absence of any enantiomeric excess or enantiomerically enriched isomer of DL-leucine. Also, the role of N-acetyl-DL-leucine in cognition improvement is ambiguous.

Further successive studies in models of vertigo on the individual enantiomers have revealed that the therapeutic effects of N-acetyl-DL-leucine are due to the L-enantiomer. Studies of a rat model of unilateral labyrinthectomy revealed that N-acetyl-L-leucine, not N-acetyl-D-leucine, is the pharmacologically active substance that improves central vestibular compensation. Furthermore, a study in a unilateral vestibular neurectomy cat model suggested that N-acetyl-L-leucine is the enantiomer that leads to a significant acceleration of the vestibular compensation process, most likely acting on vestibular nuclei neurons.

N-acetyl-L-leucine has also been demonstrated to reduce neuroinflammation in the cerebellum. In vivo studies in a mouse model for traumatic brain injury demonstrate that a treatment with N-acetyl-L-leucine improves lysosome-related autophagy flux and thereby restores its neuroprotective function in the cortices after traumatic brain injury. This is expected to lead to the attenuation and restrict neuronal cell death, hence improving neurological function. [Fields et al. *Trials* (2021) 22:84]

Therefore, there is a need for a certain neuroactive nutritional enantiomerically enriched composition that affords remedy in treatment of vestibular associated neurodegenerative diseases.

It has been found that uridine is a neuroactive molecule, which is involved in the regulation of certain neural functions apart from its role in pyrimidine metabolism. Uridine improves memory function and influences neuronal plasticity via its actions on membrane formation. Further uridine, as a dietary component, is not toxic and has access to the brain from the plasma through transporters, which makes it an appealing lead molecule for the development of drugs with central site of action.

Further, it is reported that chronic administration of uridine monophosphate (UMP) ameliorates the impairment of hippocampal-dependent memory in impoverished rats. [*J Nutr.* 2006 November; 136(11):2834-7]

U.S. Pat. No. 8,518,882B2 is directed to methods for ameliorating hippocampal dysfunction and improving or inhibiting decline in intelligence or cognitive or hippocampal-dependent memory of a subject and of increasing synthesis and release of neurotransmitters, neurite outgrowth, and levels of neurofilament proteins in the brain and central nervous system (CNS) of a subject, by administering to the subject a uridine, an acyl derivative thereof, a uridine phosphate, uracil, or a salt thereof.

Further, U.S. Pat. No. 4,960,759A discloses use of uridine for the protection of the cholecystokinin level in the brain tissue. Cholecystokinin is a peptide hormone of the gastrointestinal system responsible for stimulating the digestion of fat and protein.

Likewise, WO2013049686A1 relates to uridine diphosphate (UDP) derivatives, compositions in treating neuronal disorders, including neurodegenerative disorders (e.g., Alzheimer's disease) and traumatic CNS injury, as well as pain.

Further, it is reported that oral administration of a combination of uridine and docosahexaenoic acid (DHA) enhances the synapse formation [Wurtman, R. J., Cansev, M. & Ulus, I. H. Synapse formation is enhanced by oral administration of uridine and DHA, the circulating precursors of brain phosphatides. *J Nutr Health Aging* 13, 189-97 (2009). https://doi.org/10.1007/s12603-009-0056-3]

In view of the prior art, there is an immediate need to develop a therapeutic approach to manage vestibular disorders along with cognitive dysfunctions in patients. Considering this, the inventors of the present invention have been motivated to develop potential therapies which manage vestibular disorders and improve cognitive function where the effective combination of therapeutically active enriched isomer of acetylated derivative of a natural essential amino acid and brain-boosting supplement are employed. Accordingly, the inventors of the present invention have performed experiments and developed a nutritional composition which gives synergistic effect for treating vestibular and neurodegenerative diseases without any severe adverse reaction.

OBJECTIVES OF THE INVENTION

The primary objective of the present invention is to provide synergistic nutritional compositions for treating vestibular linked neurodegenerative diseases.

Another objective of the present invention is to provide a synergistic composition of nutrients for treating vestibular associated cognitive dysfunction in a subject in need thereof.

A further objective of the present invention is to provide a synergistic combination of therapeutically active vestibular suppressants and cognitive enhancers for rapid recovery in vestibular compensation with improved synaptic and neuronal plasticity.

Another objective of the present invention is to provide a synergistic nutrient based and isomeric remedy for treating vestibular associated neurodegenerative disorders through site specific action, with no side effects.

SUMMARY OF THE INVENTION

To meet the above objectives, the inventors of the present invention carried out experiments to establish significant therapeutic effects of the active ingredients or amino acids or nucleotides or nutrients present in the composition for improving vestibular and cognitive function in a subject in need thereof in safer way.

In an aspect, the present invention relates to synergistic nutraceutical compositions comprising therapeutically active nutrients along with pharmaceutically acceptable carriers for treating vestibular associated neurodegenerative diseases.

In another aspect the present invention provides synergistic nutraceutical compositions comprising enantiomerically enriched acetylated derivative of amino acid along with a cognitive enhancing agent i.e., nucleotide in a suitable weight ratio.

In another aspect, the present invention relates to synergistic nutraceutical compositions comprising a combination of N-acetyl-DL-leucine enantiomerically enriched with L-leucine and uridine monophosphate (UMP) in a specific weight ratio.

In another aspect, the present invention relates to synergistic nutraceutical compositions optionally comprising a metal chelating agent to eliminate neurotoxicity.

In a further aspect, the present invention provides a synergistic composition for improving vestibular associated neurodegenerative diseases comprising administration of specific combination of N-acetyl-DL-leucine enriched with L-leucine and uridine monophosphate (UMP); wherein the N-acetyl-DL-leucine enriched with L-leucine modulates the activity of central vestibular neurons by normalizing the membrane potential of depolarized or hyperpolarized neurons; while uridine monophosphate (UMP) simultaneously or subsequently enhances receptor (neurogenesis), and synapse (synaptogenesis) densities which act in synergy to improve learning acquisition and retention of spatial memory by promoting synaptic membrane and dendritic spine formation. Additionally, a metal chelating agent is added to eliminate neurotoxicity induced by mobile heavy metals.

In yet another aspect, the present invention relates to synergistic nutritional compositions comprising a combination of N-acetyl-DL-leucine enantiomerically enriched with L-leucine and uridine monophosphate (UMP), wherein N-acetyl-DL-leucine enriched with L-leucine is present in a range of 1-1500 mg and uridine monophosphate (UMP) is present in a range of 1-1000 mg along with pharmaceutically acceptable excipients/carriers. Optionally, metal chelating agent is present in a range of 1 to 500 mg of the total composition.

In yet one more aspect, the present invention discloses a synergistic nutritional composition useful for treating dizziness, imbalance, vertigo tinnitus hearing loss, brain fog, vision impairment, cognitive changes, Alzheimer's disease (AD), progressive supranuclear palsy (PSP), frontotemporal dementia (FTD), motor neurone disease (MND), multiple system atrophy (MSA), and Parkinson's disease (PD).

Abbreviations

NADLL: N-Acetyl-DL-leucine
DL: Dextrorotation Levorotation/Racemic mixture/Racemate
UMP: Uridine monophosphate
PSP: Progressive supranuclear palsy
AD: Alzheimer's disease
FTD: Frontotemporal dementia
MND: Motor neurone disease
MSA: Multiple system atrophy
PD: Parkinson's disease
BPPV: benign paroxysmal positional vertigo
NIDCD: National Institute on Deafness and Other Communication Disorders
ADL: activities of daily living
CNS: central nervous system
DHA: docosahexaenoic acid
EE: enantiomeric excess
PC: phosphatidylcholine
CDP-choline: cytidine diphosphate-choline
Ach: acetylcholine
CRP: C-reactive protein
HPC: hydroxypropyl cellulose
HPMC: hydroxypropyl methyl cellulose
PVP: polyvinylpyrrolidone
PEG: polyethylene glycol
BHA: butylated hydroxyanisole
BHT: butylated hydroxytoluene
SMB: sodium metabisulfite
PG: propyl gallate
CYS: cysteine

DETAILED DESCRIPTION OF THE INVENTION

Figure 1:
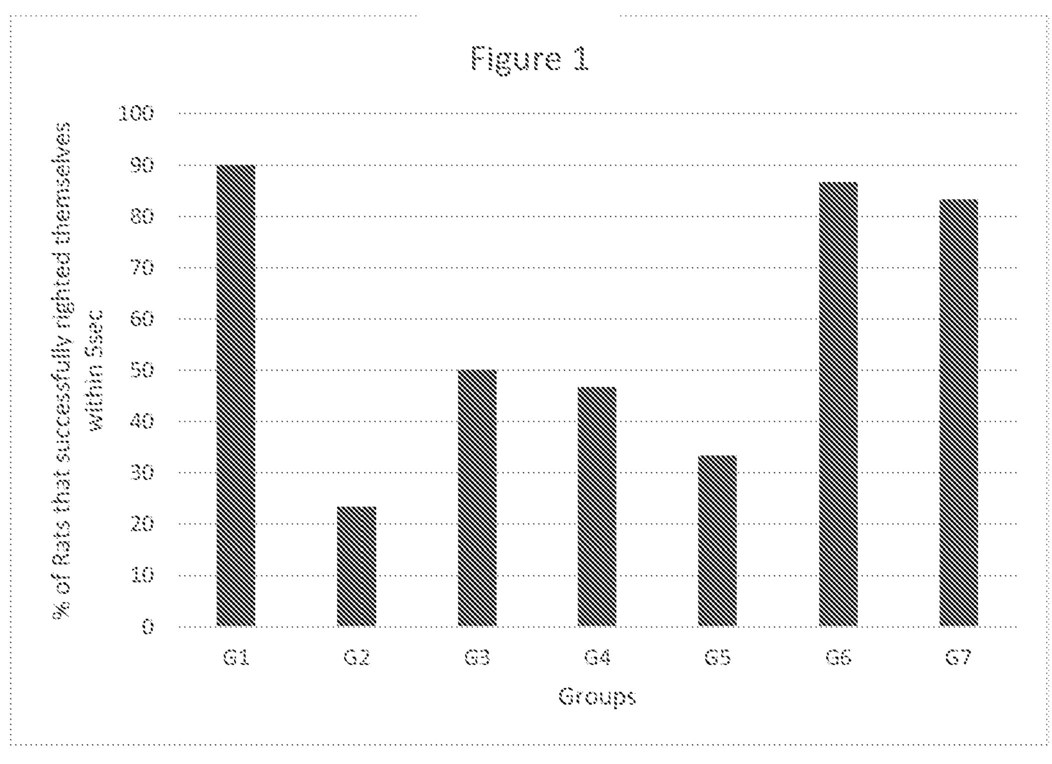
FIG. 1 illustrates air righting reflex (% of rats that successfully righted themselves within 5 seconds) G1: Normal Control, G2: Disease Control, G3: Reference Standard, G4: NADLL enriched with L-leucine, G5: UMP, G6: NADLL+UMP (Low Ratio), G7: NADLL+UMP (High Ratio).

The invention will now be described in detail in connection with certain preferred and optional embodiments, so that various aspects thereof may be more fully interpreted and comprehended. However, any skilled person or artisan will appreciate the extent to which such embodiments could be generalized in practice.

It is further to be understood that all terminology used herein is for the purpose of describing particular embodiments only and is not intended to be limiting in any manner or scope. Unless defined otherwise, all technical and scientific expressions used herein have the same meaning as commonly understood by one of ordinary skill in the art to which embodiments of the invention pertain.

In describing and claiming the embodiments of the present invention, the following terminology will be used in accordance with the definitions set out below which are known in the state of art.

The singular forms "a" "an" and "the" include plural reference unless the context clearly dictates otherwise. Also, the term "composition" does not limit the scope of the invention for multiple compositions that can be illustrated for best mode of the invention.

The term "pharmaceutically/nutraceutically acceptable salt" as used herein, represents those salts which are within the scope of sound medical judgment, are suitable for use in contact with the tissues of humans and animals without undue toxicity, irritation, allergic response and the like and are commensurate with a reasonable benefit/risk ratio. Particularly, the term "pharmaceutically-acceptable salts" refers to relatively non-toxic, inorganic and organic acid addition salts of compounds, amino acid salt, sugar based salt, alkali or alkaline earth metal salts, as well as solvates, co-crystals, polymorphs and the like of the salts.

All modifications and substitutions that come within the meaning of the description and the range of their legal equivalents are to be embraced within their scope. A description using the transitional phrase "comprising" allows the inclusion of other elements to be within the scope of the invention.

The term "enantiomeric excess" (EE) relates to the excess of one enantiomer over the other in a mixture of enantiomers. The term "enantiomerically enriched" or enantioenriched defines a sample of a chiral substance whose enantiomeric ratio is greater than 50:50 but less than 100:0.

In a preferred embodiment, the invention provides a synergistic nutritional composition comprising an exogenous blend of N-acetyl-DL-leucine enantiomerically enriched with L-leucine and uridine monophosphate (UMP) along with pharmaceutically acceptable carriers.

In another embodiment, the invention provides a synergistic nutritional composition optionally comprising metal chelating agent. The metal chelating agent is used to eliminate neurotoxicity.

In another embodiment, the invention provides a synergistic nutritional composition for treating vestibular associated neurodegenerative diseases.

The term "neurodegenerative diseases" is defined as a heterogeneous group of disorders that are characterized by the progressive degeneration of the structure and function of the central nervous system or peripheral nervous system. Neurodegenerative diseases often result in a combination of cognitive and motor deficits that affect an individual's ability to perform daily tasks.

The term "cognitive ability" is defined as a mental capability that involves the ability to reason, plan, solve problems, think abstractly, comprehend complex ideas, learn quickly and learn from experience.

The term "cognitive dysfunction" can be used interchangeably with cognitive impairment, cognitive imbalance, cognitive decline, cognitive deficit, cognitive problems, cognitive instability, cognitive disorders, cognitive issues, cognitive ageing, neurocognitive disorder, synaptic loss and like thereof.

Neurodegenerative diseases are those that affect neurons. The degenerative process can involve the progressive loss of neuronal structure, the progressive loss of neuronal function, or progressive neuron cell death. Such progressive neurodegeneration often results in physical disability and mental deterioration. Many neurodegenerative diseases are severely progressive and unremitting, and there are few, if any, curative treatments.

In a particular embodiment, the invention provides a biologically active composition which is composed of a synergistic combination of N-acetyl-DL-leucine (NADLL) enantiomerically enriched (EE) with L-leucine and uridine monophosphate (UMP) present in therapeutically effective amounts. The composition exhibits significant vestibular and neurodegenerative regulating/stabilizing effect with enhanced bioavailability, solubility, and therapeutic efficacy.

The improvement in cognitive function is attributed to the synergistic effect of nutrients present in the composition; wherein N-acetyl-DL-leucine enantiomerically enriched with L-leucine modulates the activity of central vestibular neurons by normalizing the membrane potential of depolarized or hyperpolarized neurons; while UMP acts in synergy to improve learning acquisition and retention of spatial memory by promoting synaptic membrane and dendritic spine formation.

In another embodiment, the invention provides a nutritional combination, wherein the neurotoxicity is eliminated by optionally using metal chelating agent.

According to the invention, N-acetyl-DL-leucine enantiomerically enriched (EE) with L-leucine modulates the activity of central vestibular neurons by normalizing the membrane potential of depolarized or hyperpolarized neurons.

N-acetyl-DL-leucine also referred to as N-Acetyl-leucine, is chemically known as (2S)-2-acetamido-4-methylpentanoic acid; (E)-N-(1-Hydroxyethylidene)-L-leucine; (S)—N-acetyl-leucine. Its molecular formula is $C_8H_{15}NO_3$. The chemical structure of N-Acetyl-DL-leucine enantiomerically enriched (EE) with L-leucine is represented below as Formula I.

Formula I

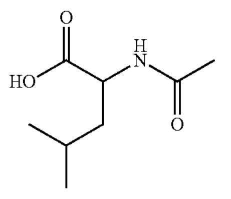

N-acetyl-L-leucine is chemically derived from the essential amino acid leucine by addition of an acetyl group. Addition of acetyl or carbon groups or chains to small molecules change their properties quite radically. The European Journal of Pharmacology [769(2015) 342-349] suggests that only the L-enantiomer shows better therapeutic effect on postural compensation than D-enantiomer. Hence, the inventors of the present invention have used N-acetyl-DL-leucine enantiomerically enriched with L leucine.

In another embodiment, the invention provides synergistic nutritional composition comprising N-acetyl-DL-leucine wherein D-leucine is present in a range of 5% to 45% and L-leucine is present in a range of 55% to 95% in the racemic mixture of N-acetyl-DL-leucine.

In another embodiment, the invention provides synergistic nutritional composition comprising N-acetyl-DL-leucine wherein D-leucine to L-leucine ratio ranges from 45:55; 40:60; 35:65; 30:70; 25:75; 20:80; 15:85; 10:90; 5:95.

In further embodiment, the invention provides synergistic nutritional composition, wherein N-acetyl-DL-leucine (EE) with L-leucine modulates the activity of central vestibular neurons by normalizing the membrane potential of depolarized or hyperpolarized neurons. In addition, N-acetyl-DL-leucine also changes the regional cerebral glucose metabolism after vestibular damage.

The N-acetyl-DL-leucine according to the present invention demonstrates a superior effect on the stimulation and/or restoration of the membrane potential of depolarized or hyperpolarized neurons. The effect is mediated by modulation of the ion channel activity. Further N-acetyl-DL-leucine also has effects on cerebellar neurons where the binding of N-acetyl-DL-leucine to a stereospecific site of a receptor or enzyme, is upregulated during vestibular compensation. N-acetyl-L-leucine, which is a branched-chain amino acid, may modulate glutamate neurotransmission in the cerebellum via the branched-chain amino acid transferases.

In yet another embodiment, the present invention provides a synergistic nutritional composition comprising a therapeutically effective amount of N-acetyl-DL-leucine enriched with L-leucine along with pharmaceutically acceptable salts thereof, wherein N-acetyl-DL-leucine enriched with L-leucine is present in a range of 1-1500 mg of the total composition. Particularly, N-acetyl-DL-leucine enriched with L-leucine is present in a range of 1-1000 mg of the total composition.

In another embodiment, the synergistic effect of the nutritional combination for treating neurodegenerative diseases is achieved by concomitant administration of another moiety, particularly a nucleotide called uridine monophosphate that effectively acts in a synergistic manner to improve learning acquisition and retention of spatial memory by promoting synaptic membrane and dendritic spine formation.

Uridine monophosphate (UMP), also known as 5'-uridylic acid (conjugate base uridylate), is a nucleotide that is used as a monomer in RNA. It is an ester of phosphoric acid with the nucleoside uridine and is referred to as [(2R,3S,4R,5R)-5-(2,4-Dioxopyrimidin-1-yl)-3,4-dihydroxyoxolan-2-yl] methyl dihydrogen phosphate, Uridine 5'-monophosphate or 5'-UMP. Its molecular formula is $C_9H_{13}N_2O_9P$. The chemical structure of uridine monophosphate (UMP) is represented below as Formula II.

Formula II

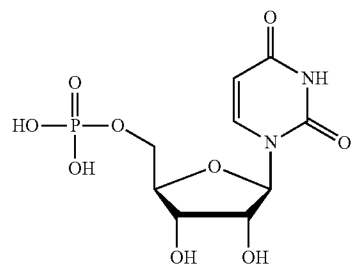

In another embodiment, the invention discloses a nutritional composition, wherein the uridine monophosphate salt is uridine 5'-monophosphate disodium salt. In another embodiment, the invention discloses a nutritional composition, wherein uridine monophosphate enhances receptor (neurogenesis), and synapse (synaptogenesis) densities by increasing the level of citicoline.

Memory is largely dependent on neuroplasticity which is associated with the ability to learn and form memories. This process of turning experiences into memories relies on the growth of new neurons (neurogenesis), new synapses (synaptogenesis), dendrite formation, and network reorganization. Uridine is a major building block for the synthesis of neurons and synapses. It enhances the growth of neurites, which are projections from neurons that facilitate connections with other neurons. The decreased number of cortical synapses leads to cognitive memory impairment. UMP treatment promotes synaptogenesis. The formation of a new synapse (by, for example, hippocampal neurons that use glutamate as their neurotransmitter) is initiated by the coming together of a presynaptic terminal and a dendritic spine. Thus, the availability of dendritic spines is an important factor controlling the rate of synaptogenesis.

Further new neurons (neurogenesis) are encased in a phospholipid layer made up partly of phosphatidylcholine (PC). PC is made from cytidine diphosphate-choline (CDP-Choline) which is produced with the help of uridine. Uridine supplementation gives the brain the ability to create more phospholipids by providing an abundance of CDP-Choline, which yields in new and stronger neurons.

Uridine is a precursor to the formation of CDP-Choline which is a precursor to the formation of phosphatidylcholine (PC). PC separates into choline and sphingomyelin in brain. Choline is then available to form essential neurotransmitter acetylcholine (ACh). An optimal ACh level is crucial for cognitive performance. Thus, the present composition maintains optimal ACh level.

In a further embodiment, the present invention provides a synergistic effect of uridine to improve cognitive function by increasing receptor (neurogenesis), and synapse (synaptogenesis) densities by modulating acetylcholine levels that improve cellular phospholipid membrane health and consequently boost learning and memory ability.

In another embodiment, the present invention provides a method of increasing the release of a neurotransmitter into a synapse, which comprises contacting a neural cell adjacent to the synapse with a uridine or salts or derivatives or metabolites thereof, thereby increasing a release of the neurotransmitter into a synapse.

In another embodiment, the synergistic nutritional composition comprises a therapeutically effective amount of UMP along with pharmaceutically acceptable salts thereof, wherein UMP is present in a range of 1-1000 mg of the total composition. In a preferred embodiment, UMP is present in a range of 1-500 mg of the total composition.

In a further optional embodiment, the invention provides a synergistic combination for treatment of vestibular and neurodegenerative diseases, wherein a metal chelating agent is optionally added to eliminate neurotoxicity. It further helps to enhance the bioavailability of the instant active ingredients.

In another preferred embodiment the invention provides a novel, stable and potent synergistic nutritional composition comprising therapeutically active exogenous combination of an effective amount of N-acetyl-DL-leucine enantiomerically enriched with L-leucine and uridine monophosphate (UMP) which are present in a weight ratio of 1:0.002 to 1:0.8 along with pharmaceutically acceptable excipients.

In yet another preferred embodiment, the invention provides novel and stable nutritional compositions for improving vestibular associated neurodegenerative diseases comprising exogenous blend of N-acetyl-DL-leucine enantiomerically enriched with L-leucine and uridine monophosphate (UMP) present in the weight ratio of 1:0.002 to 1:0.8, along with pharmaceutically acceptable excipients, wherein the two active ingredients act synergistically to improve vestibular related cognitive function.

In yet another embodiment the invention provides novel and stable nutritional compositions for improving vestibular associated neurodegenerative diseases comprising exogenous blend of N-acetyl-DL-leucine enantiomerically enriched with L-leucine and uridine monophosphate, wherein the N-acetyl-DL-leucine enantiomerically enriched with L-leucine and the uridine monophosphate are present in a white crystalline form.

In yet another preferred embodiment, the invention provides novel and stable nutritional compositions for improving vestibular associated neurodegenerative diseases comprising exogenous blend of N-acetyl-DL-leucine enantiomerically enriched with L-leucine and uridine monophosphate (UMP) in weight ratio of 1:0.002 to 1:0.8, along with pharmaceutically acceptable excipients, wherein the N-Acetyl-DL-leucine enriched with L-leucine modulates the activity of central vestibular neurons by normalizing the membrane potential of depolarized or hyperpolarized neurons; concurrently uridine monophosphate (UMP) enhances receptor (neurogenesis), and synapse (synaptogenesis) densities which act in synergy to improve learning acquisition and retention of spatial memory by promoting synaptic membrane and dendritic spine formation.

In one more embodiment, the invention provides potent and stable synergistic nutritional composition comprising N-Acetyl-DL-leucine enriched with L-leucine present in a range of 50% to 98% by weight of the total composition.

In another embodiment, the invention provides potent and stable synergistic nutritional composition comprising uridine monophosphate (UMP) which is present in a range of 0.1% to 35% by weight of the total composition.

In another embodiment, the invention provides potent and stable synergistic nutritional composition useful for treating vestibular associated neurodegenerative diseases.

In another embodiment, the invention provides the nutritional composition wherein the N-acetyl-DL-leucine containing L-leucine with 10% to 90% enantiomerically excess. Moreover, the L-leucine is present in the range of 55% to 95% in the racemic mixture, by weight of the total N-acetyl-DL-leucine.

The term "therapeutically effective amount" denotes an amount that reduces the risk, potential, possibility or occurrence of a disease or disorder, or provides advanced alleviation, mitigation, and/or reduction or restoration or modulation, regulation of at least one indicator/biomarker (e.g., blood or serum C-reactive protein (CRP) level, and/or minimize at least one clinical symptom related to vestibular dysfunction and neurodegenerative diseases.

The term "subject in need thereof" pertains to a subject, preferably a mammal, more preferably human suffering from or suspected to be suffering from vestibular dysfunctions associated neurodegenerative disorders.

In the context of the present invention, the term "treatment" refers to alleviate, mitigate, prophylaxis, attenuate, manage, regulate, modulate, control, minimize, lessen, decrease, down regulate, up regulate, moderate, inhibit, restore, suppress, reverse, limit, block, decrease, prevent, inhibit, stabilize, ameliorate or cure, heal vestibular dysfunctions and neurodegenerative disorders.

Notably, the instant synergistic composition is non-hazardous, non-toxic, food ingredient and safe for human consumption without any adverse effects, therefore the present nutritional composition is also used as preventive therapy/adjuvant therapy/add-on therapy/combination/adjunctive therapy in a subject in need thereof.

Certain compounds of the present invention exist in unsolvated forms as well as solvated forms, including hydrated forms. Further some compounds of the present invention exist in multiple crystalline or amorphous forms ("polymorphs"). Compounds of the invention are formulated in geometric or enantiomeric or stereoisomeric forms.

As used herein, the term "pharmaceutically acceptable carriers, diluents or excipients" is purported to mean, without limitation, any adjuvant, carrier, excipient, sweetening agent, diluents, preservative, dye/colorant, flavor enhancer, surfactant, wetting agent, dispersing agent, suspending agent, stabilizer, isotonic agent, solvent, emulsifier, or encapsulating agent, encapsulating polymeric delivery systems or polyethyleneglycol matrix, which is acceptable for use in the subject, preferably humans. Excipients also include, for example: antiadherents, antioxidants, binders, coatings, compression aids, disintegrants, dyes (colors), emollients, emulsifiers, fillers (diluents), film formers or coatings, fragrances, glidants (flow enhancers), lubricants, preservatives, sorbents, suspending or dispersing agents, sweeteners, surfactant, anticaking agent, food additives, or waters of hydration, salts.

In another embodiment, the invention relates to synergistic nutritional compositions prepared in a manner well known in the pharmaceutical art, and administered by a variety of routes, depending upon whether local or systemic treatment is desired and upon the area to be treated. The preferable route of administration includes but is not limited to sublingual, rectal, topical, parenteral, nasal or oral.

In one embodiment, the present synergistic medicinal composition is administered to a subject in need thereof, in the form which is suitable for oral use, such as a tablet, capsule (in the form of delayed release, extended release, sustained release, enteric coated release); hard gelatin capsules, soft gelatin capsules in an oily vehicle, veg capsule, hard or soft cellulose capsule, granulate for sublingual use, effervescent or carbon tablets, aqueous or oily solution, suspension or emulsion, encapsulate, matrix, coat, beadlets, nanoparticles, caplet, granule, particulate, agglomerate, spansule, chewable tablet, lozenge, troche, solution, suspension, rapidly dissolving film, elixir, gel, tablets, pellets, granules, capsules, lozenges, aqueous or oily solutions, suspensions, emulsions, sprays or reconstituted dry powdered form with a liquid medium or syrup; for topical use including transmucosal and transdermal use, such as a cream, ointment, gel, aqueous or oil solution or suspension, salve, parch or plaster; for nasal use, such as a snuff nasal spray or nasal drops; for vaginal or rectal use, such as a suppository; for administration by inhalation, such as a finely divided powder or a liquid aerosol; for sub-lingual or buccal use, such as a tablet, capsule, film, spray.

In a further embodiment, the composition is formulated for parenteral use including intravenous, subcutaneous, intramuscular, intravascular, infusion, intraperitoneal, intracerebral, intracerebroventricular, or intradermal routes of administration.

Formulations of the present invention suitable for oral administration can be presented as discrete units such as capsules (e.g., soft-gel capsules), cachets or tablets each containing a predetermined amount of the active ingredient; as a powder or granules; as a solution or a suspension in an aqueous liquid or a non-aqueous liquid, syrup; or as an oil-in-water liquid emulsion or a water-in-oil liquid emulsion. The active ingredients can also be presented in the form paste, nutritional bar, energy bars (candy bars), powder, granule sachet.

Further, the present composition can be formulated in the form of age-appropriate paediatric oral dosage forms such as syrup, minitablets, chewable formulations, orodispersible films, orodispersible tablets and bioadhesive buccal tablets. It can also be prepared in the form of snack, chocolate bars or other confectionery food products.

In another embodiment, the synergistic composition of the present invention is non-toxic, cost effective, enriched with nutrients or biomolecules, and provides safeguard against problems associated with neurotransmission without any adverse effect.

In another embodiment of the invention, the diluents are selected from starches, hydrolyzed starches, partially pregelatinized starches, anhydrous lactose, cellulose powder, lactose monohydrate, sugar alcohols such as sorbitol, xylitol and mannitol, silicified microcrystalline cellulose, ammonium alginate, calcium carbonate, calcium lactate, dibasic calcium phosphate (anhydrous/dibasic dehydrate/tribasic), calcium silicate, calcium sulphate, cellulose acetate, corn starch, pregelatinized starch, dextrin, β-cyclodextrin, methylated-β-cyclodextrin, dextrates, dextrose, erythritol, ethyl cellulose, fructose, fumaric acid, glyceryl palmitostearate, magnesium carbonate, magnesium oxide, maltodextrin, maltose, medium-chain triglycerides, polydextrose, polymethacrylates, sodium alginate, sodium chloride, sterilizable maize, sucrose, sugar spheres, talc, trehalose, xylitol, vehicles like petrolatum, dimethyl sulfoxide and mineral oil or the like.

In some embodiment of the invention, the diluent in the composition/formulation is present in a range of 1% to 30% by weight of the total composition/formulation.

In yet another embodiment of the invention, the binder is selected from disaccharides such as sucrose, lactose, polysaccharides and their derivatives like starches, cellulose, or modified cellulose such as microcrystalline cellulose and cellulose ethers such as hydroxypropyl cellulose (HPC); hydroxypropyl methyl cellulose (HPMC); sugar alcohols such as xylitol, sorbitol, or mannitol; protein like gelatin; synthetic polymers such as polyvinylpyrrolidone (PVP), polyethylene glycol (PEG), starch, acacia, agar, alginic acid, calcium carbonate, calcium lactate, carbomers, carboxymethylcellulose sodium, carrageenan, cellulose acetate phthalate, chitosan, co-povidone, corn starch, pregelatinized starch, cottonseed oil, dextrates, dextrin, dextrose, ethyl cellulose, guar gum, hydrogenated vegetable oil, mineral oil, hydroxyethyl cellulose, hydroxymethyl cellulose, hydroxyl ethyl methyl cellulose, hydroxypropyl cellulose, inulin, cellulose, methyl cellulose, polyvinylpyrrolidone and polyethylene glycol, lactose, liquid glucose, hypromellose, magnesium aluminum silicate, maltodextrin, maltose, methylcellulose, microcrystalline cellulose, pectin, poloxamer, polydextrose, polymethacrylates, povidone, sodium alginate, stearic acid, sucrose, sunflower oil, various animal vegetable oils, and white soft paraffin, paraffin, flavorants, colorants and wax.

In further embodiment of the invention, the binder in the composition/formulation is present in a range of 0.1 to 40% by weight of the composition/formulation.

In some embodiment, the antioxidant is selected from tocopherol (vitamin E), sesamol, guaiac resin, mehionine, beta-carotene, lycopene, lutein, zeaxanthin, butylated hydroxyanisole (BHA), butylated hydroxytoluene (BHT), sodium ascorbate, sodium metabisulfite (SMB), 1-carnosine, propyl gallate (PG), tertiary butyl hydroquinone, cysteine (CYS), citric acid, tartaric acid, phosphoric acid and ascorbic acid.

In some embodiment of the invention, the amount of antioxidant in the composition/formulation is present in the range of 0.1 to 10% by wt. of the composition/formulation.

In another embodiment of the invention, the lubricant is selected from magnesium stearate, zinc stearate, calcium stearate, glycerin monostearate, glyceryl behenate, glyceryl palmitostearate, hydrogenated castor oil, hydrogenated vegetable oil, light mineral oil, magnesium lauryl sulphate, medium-chain triglycerides, mineral oil, myristic acid, palmitic acid, poloxamer, polyethylene glycol, sodium benzoate, sodium chloride, sodium lauryl sulphate, sodium stearyl fumarate, stearic acid, talc, potassium, or sodium benzoate or the like.

In some embodiment of the invention, the lubricant in the composition/formulation is present in a range of 0.1% to 10.0% by weight of the total composition/formulation.

In another embodiment of the invention, the solubilizing agent is selected from polysorbate 80, sodium lauryl sulphate, anionic emulsifying wax, nonionic emulsifying wax, glyceryl monooleate, phospholipids, polyoxyethylene alkyl ethers, polyoxyethylene castor oil derivatives, polyoxyethylene sorbitan fatty acid esters, polyoxyethylene stearates, polyoxylglycerides, sorbitan esters, triethyl citrate, vitamin E, polyethylene glycol succinate, microcrystalline cellulose, carboxymethylcellulose sodium, diethanolamine, ethylene glycol palmitostearate, glycerin monostearate, hypromellose, hypromellose, acetate succinate, lecithin, polyethylene alkyl ethers, aluminum oxide, poly(methylvinyl ether/maleic anhydride), calcium carbonate, crospovidone, cyclodextrins, fructose, hydroxpropyl betadex, oleyl alcohol, povidone, benzalkonium chloride, benzethonium chloride, benzyl alcohol, benzyl benzoate, cetylpyridinium chloride, inulin, meglumine, poloxamer, pyrrolidone, sodium bicarbonate, starch, stearic acid, sulfobutylether beta cyclodextrin, tricaprylin, triolein, docusate sodium, glycine, alcohol, self-emulsifying glyceryl monooleate, cationic benzethonium chloride, cetrimide, xanthan gum, lauric acid, myristyl alcohol, butylparaben, ethylparaben, 15 methylparaben, propylparaben, sorbic acid or the like.

In another embodiment of the invention, the amount of solubilizing agent or surfactant in the composition/formulation ranges from 0.1% to 10% by weight of the composition/formulation.

In a preferred embodiment of the invention, the solubilizing agent or surfactant is present in a range of 0.1% to 5.0% by weight of the composition/formulation.

In some embodiment of the invention, the glidant is selected from colloidal silicon dioxide, magnesium stearate, fumed silica (colloidal silicon dioxide), starch, talc, calcium phosphate tribasic, cellulose powdered, hydrophobic colloidal silica, magnesium oxide, zinc stearate, magnesium silicate, magnesium trisilicate, silicon dioxide or the like.

In another embodiment of the invention, the glidant in the composition/formulation is present in a range of 0.1% to 5.0% by weight of the total composition/formulation.

In some embodiment of the invention, the stabilizers are selected from the group consisting of alginate, agar, carrageen, gelatin, guar gum, gum arabic, locust bean gum, pectin, starch, xanthan gum, trehalose and likewise.

In some embodiment of the invention, the stabilizer in the composition/formulation is present in a range of 0.1% to 8.0% by weight of the total composition/formulation.

In some embodiment of the invention, the plasticizers are added to coating formulations selected from the group propylene glycol, glycerol, glyceryl triacetate (triacetin), triethyl citrate, acetyl triethyl citrate, diethyl phthalate, actetylated monoglycerides, castor oil, mineral oil and like thereof.

In some embodiment of the invention, the plasticizer in the composition/formulation is present in a range of 0.1% to 5.0% by weight of the total composition/formulation.

In some embodiment of the invention, the solvent is selected from water, alcohol, isopropyl alcohol, propylene glycol, mineral oil, benzyl alcohol, benzyl benzoate, flavored glycol, carbon dioxide, castor oil, corn oil (maize), cottonseed oil, dimethyl ether, albumin, dimethylacetamide, ethyl acetate, ethyl lactate, medium-chain triglycerides, methyl lactate, olive oil, peanut oil, polyethylene glycol, polyoxyl, castor oil, propylene carbonate, pyrrolidone, safflower oil, sesame oil, soybean oil, sunflower oil, water-miscible solvents, organic polar or non-polar solvents or mixtures thereof.

In a preferred embodiment of the invention, the solvent in the composition/formulation is used in a quantity sufficient to make the weight of the composition/formulation 100% by weight.

The additional additives include a polymer, a plasticizer, a sweetener, and a powdered flavor, a preservative, a colorant, a surfactant, and other excipients. The powdered flavor composition includes a flavourant associated with a solid carrier. Coating materials such as synthetic polymers, shellac, corn protein (zein) or other polysaccharides, gelatin, fatty acids, waxes, shellac, plastics, and plant fibers and like thereof are used.

In a preferred embodiment of the invention, the additives are used in a range of 1 to 20% w/w of unit dose.

In yet another embodiment, the invention provides a synergistic nutritional composition comprising a therapeutic blend of N-acetyl-DL-leucine (NADLL) enantiomerically enriched (EE) with L-leucine and uridine monophosphate (UMP) present in therapeutically effective amounts along with pharmaceutical excipients, wherein the pharmaceutical excipients are selected from a diluent, a binder, a lubricant, a glidant, an additive, a surfactant, a stabilizer or mixtures thereof.

In a preferred embodiment, the invention provides the novel and stable nutritional composition wherein the pharmaceutically acceptable excipients are selected from a group consisting of the diluent is present in a range of 1 to 30%; the binder present is present in a range of 0.1 to 25%; the lubricant is present in a range of 0.1 to 10.0%; the glidant is present in a range of 0.1 to 5.0%; the additive is present in a range of 1 to 10%; the surfactant is present in a range of 0.1 to 5.0%; the stabilizer is present in a range of 0.1 to 5.0%; %; the antioxidant is present in a range of 0.1 to 5.0%; and the plasticizer is present in a range of 0.1 to 5.0%; by weight of total composition.

In another preferred embodiment, the present medicinal composition/formulation is formulated for oral administration. Specifically, the solid medicinal compositions, are in the form of tablets, capsules, pills, hard capsules filled with liquids or solids, soft capsules, sachets, powders, granules, suspensions, solutions, or modified release formulations.

In further embodiment compositions containing compounds of the invention, can be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof.

The magnitude of a prophylactic or therapeutic dose typically varies with the nature and severity of the condition to be treated and the route of administration. The dose, and perhaps the dose frequency, will also vary according to the age, body weight and response of the individual patient.

In general, the total daily dose (in single or divided doses) ranges from about 1 mg per day to about 2500 mg per day, preferably about 10 mg per day to about 1000 mg per day. In some embodiments, the total daily dose can range from about 5 mg to about 4000 mg per day, and preferably about 5 mg to about 2000 mg per day.

In certain embodiments, the invention provides the potent synergistic medicinal composition wherein the effective unit dose for an oral administration is formulated in a range of 10 to 1000 mg.

It is further recommended that children, patients over 60 years old, initially receive low doses and that the dosage be titrated based on individual physiological responses and/or pharmacokinetics. It can be necessary to use dosages outside these ranges in some cases, as will be apparent to those in the art. The present composition can be used as infant formula as well as adult formula by varying the concentration of active ingredients. Further, it is noted that the dietician or nutritionist or certified physician knows how and when to interrupt, adjust or terminate therapy in conjunction with an individual patient's response.

The use of any and all examples, or exemplary language (e.g., such as) provided herein, is intended merely to better illuminate the invention, and does not pose a limitation on the scope of the invention unless otherwise claimed.

Various other examples of compositions and modifications or adaptations thereof can be devised by a person skilled in the art after reading the foregoing preferred embodiments without departing from the spirit and scope of the invention. All such further examples, modifications and adaptations are included within the scope of the invention.

It will be appreciated by those versed in the art that the present invention makes available novel and useful nutraceutical compositions and nutraceutical acceptable salts thereof, which have neuroprotective effects in several administration forms. Also, it will be understood by those with knowledge in the dietary supplement and nutraceutical art, that many embodiments of this invention may be made without departing from the spirit and scope of the invention, and the invention is not to be construed as limited, as it embraces all equivalents therein.

The invention may be further illustrated by the following examples, which are for illustrative purposes only and should not be construed as limiting the scope of the invention in anyway. The present disclosure is therefore to be considered as in all respects illustrative and not restrictive, the scope of the invention being indicated by the appended claims and examples, and all changes or alterations which come within the ambit of equivalency are intended to be encompassed therein.

EXAMPLES

Having described the basic aspects of the present invention, the following non-limiting examples illustrate specific embodiments thereof. Those skilled in the art will appreciate that many modifications may be made in the invention without changing the essence of invention.

Example-1 i. Composition 1: Synergistic blend

| Ingredient | w/w % |
|---|---|
| N-acetyl-DL-leucine enriched with L-leucine | 50 to 98% |
| Uridine monophosphate | 0.1 to 35% |

ii. Composition 2: Tablet/Capsule

| Ingredient | w/w % unit dose |
|---|---|
| N-Acetyl-DL-leucine enriched with L-leucine | 50 to 98% |
| Uridine monophosphate | 0.1 to 35% |
| Excipient | 5-20% |
| Average Weight | 100% |
| Average weight in mg | 300-500 mg |

iii. Composition 3: Tablet/Capsule

| Ingredient | w/w % unit dose |
|---|---|
| N-Acetyl-DL-leucine enriched with L-leucine | 50-98% |
| Uridine monophosphate | 0.1-35% |
| Diluents | 1-10% |
| Binders | 0.1-5% |
| Glidants | 0.1-5% |
| Lubricants | 0.1-5% |
| Stabilizers | 0.1-10% |
| Additives | 1-10% |
| Antioxidant | 0.1-5% |
| Solvents | QS |

iv. Composition 4: Tablet/Capsule

| Ingredient | mg per unit dose |
|---|---|
| N-Acetyl-DL-leucine enriched with L-leucine | 500 |
| Uridine monophosphate | 3 |
| Magnesium Stearate | 1-10 |
| Hydroxypropyl Methylcellulose | 1-10 |
| Microcrystalline Cellulose | 1-20 |
| PVP K-30 | 5-10 |
| Methylated-β-cyclodextrin | 1-10 |
| Polysorbate 20 | 1-10 |
| Sorbitol | 1-20 |
| Propylene Glycol | QS |
| Water | QS |
| Average weight | 510-600 mg |

v. Composition 5: Tablet/Capsule

| Ingredient | mg per unit dose |
|---|---|
| N-Acetyl-DL-leucine enriched with L-leucine | 100 |
| Uridine monophosphate | 50 |
| Sodium ascorbate | 2-10 |
| Microcrystalline Cellulose | 2-20 |
| Colloidal Silicon dioxide | 5-15 |
| Hydroxypropyl Methylcellulose | 2-10 |
| Triethyl citrate | 2-10 |
| PVP K-30 | 5-10 |
| Talc | 1-10 |
| Tween 80 | 1-10 |
| Mannitol | 5-20 |
| Alcohol | QS |
| Water | QS |
| Average weight | 175-260 mg |

vi. Composition 6: Tablet/Capsule

| Ingredient | mg per unit dose |
|---|---|
| N-Acetyl-DL-leucine enriched with L-leucine | 500 |
| Uridine monophosphate | 1.5 |
| Sodium alginate | 1-10 |
| Microcrystalline Cellulose | 2-20 |
| Silicon dioxide | 5-15 |
| Hydroxypropyl Methylcellulose | 2-10 |
| Stearic acid | 2-10 |
| Dibasic calcium phosphate | 1-20 |
| Pregelatinized starch | 4.5-10.5 |
| Talc | 1-10 |
| Tween 80 | 1-10 |
| Polydextrose | 5-20 |
| Water | QS |
| Average weight | 530-640 mg |

vii. Composition 7: Tablet/Capsule

| Ingredient | mg per unit dose |
|---|---|
| N-Acetyl-DL-leucine enriched with L-leucine | 250 |
| Uridine monophosphate | 3 |
| Microcrystalline Cellulose | 1-10 |
| Silicon dioxide | 1-10 |
| Ethyl Cellulose | 1-10 |
| Hydroxypropyl Methylcellulose | 1-10 |
| Magnesium Stearate | 2-10 |
| Polyvinylpyrrolidone | 1-10 |
| Talc | 1-10 |
| Polysorbate 20 | 1-10 |
| Mannitol | 1-10 |
| IPA | QS |

-continued

| vii. Composition 7: Tablet/Capsule | |
|---|---|
| Ingredient | mg per unit dose |
| Water | QS |
| Average weight | 265-350 mg |

| viii. Composition 8: Tablet/Capsule | |
|---|---|
| Ingredient | mg per unit dose |
| N-Acetyl-DL-leucine enriched with L-leucine | 50 |
| Uridine monophosphate | 25 |
| Silicon Dioxide | 1-10 |
| Medium-chain triglycerides | 1-5 |
| Microcrystalline Cellulose | 1-20 |
| Dibasic Calcium Phosphate | 1-20 |
| Magnesium Stearate | 1-10 |
| Croscarmellose sodium | 0.5-10 |
| Polyvinylpyrrolidone | 1-20 |
| Talc | 0.5-10 |
| Corn Starch | 1-10 |
| Sodium ascorbate | 1-10 |
| Propylene glycol | 1-10 |
| Water | QS |
| Average weight | 80-150 mg |

| ix. Composition 9: Tablet/Capsule | |
|---|---|
| Ingredient | mg per unit dose |
| N-Acetyl-DL-leucine enriched with L-leucine | 300 |
| Uridine monophosphate | 5 |
| Microcrystalline Cellulose | 1-10 |
| Colloidal silicon dioxide | 1-10 |
| Hydroxypropyl Methylcellulose | 1-10 |
| Magnesium Stearate | 1-10 |
| Polyvinylpyrrolidone | 1-10 |
| Calcium Phosphate | 1-10 |
| Ascorbic Acid | 1-10 |
| Polysorbate 20 | 1-10 |
| Talc | 1-5 |
| Sucrose | 1-10 |
| Mannitol | 1-10 |
| Glycerol | 1-10 |
| Average weight | 320-450 mg |

| x. Composition 10: Tablet/Capsule | |
|---|---|
| Ingredient | mg per unit dose |
| N-Acetyl-DL-leucine enriched with L-leucine | 200 |
| Uridine monophosphate | 25 |
| Microcrystalline Cellulose | 1-10 |
| Silicon dioxide | 1-10 |
| Hydroxypropyl Methylcellulose | 1-10 |
| Magnesium Stearate | 2-10 |
| Zinc Stearate | 1-5 |
| Polyvinylpyrrolidone | 1-10 |
| Mineral Oil | 1-10 |
| Sodium benzoate | 1-10 |
| Ascorbic Acid | 1-10 |
| Polysorbate 20 | 1-5 |
| Stearic acid | 1-5 |
| Dextrose | 1-10 |
| Mannitol | 1-5 |
| Water | QS |
| Average weight | 240-350 mg |

| xi. Composition 11: Tablet/Capsule | |
|---|---|
| Ingredient | mg per unit dose |
| N-Acetyl-DL-leucine enriched with L-leucine | 250 |
| Uridine monophosphate | 10 |
| Microcrystalline Cellulose | 1-10 |
| Silicon dioxide | 1-10 |
| Hydroxypropyl Methylcellulose | 1-10 |
| Magnesium Stearate | 2-10 |
| Zinc Stearate | 1-5 |
| Polyvinylpyrrolidone | 1-10 |
| Mineral Oil | 1-10 |
| Sodium benzoate | 1-10 |
| Citric Acid | 1-10 |
| Polysorbate 80 | 1-10 |
| Talc | 1-5 |
| Sucrose | 1-10 |
| Mannitol | 1-10 |
| Water | QS |
| Average weight | 275-400 mg |

| xii. Composition 12: Tablet/Capsule | |
|---|---|
| Ingredient | mg per unit dose |
| N-Acetyl-DL-leucine enriched with L-leucine | 500 |
| Uridine monophosphate | 50 |
| Microcrystalline Cellulose | 1-10 |
| colloidal Silicon dioxide | 1-10 |
| Hydroxypropyl Cellulose | 1-10 |
| Magnesium Stearate | 2-10 |
| Calcium Stearate | 1-5 |
| Polyvinylpyrrolidone | 1-10 |
| Mineral Oil | 1-10 |
| Sodium benzoate | 1-10 |
| Ascorbic Acid | 1-10 |
| Polysorbate 20 | 1-10 |
| Talc | 1-5 |
| Dextrose | 1-10 |
| Mannitol | 1-10 |
| Water | QS |
| Average weight | 560-620 mg |

The present composition is stable for 24 months under the accelerated condition [40° C., 75% RH], where the purity of the active ingredients is above 98%.

Example 2: Animal Study

"Evaluation of test substance on sodium arsanilate induced vestibular dysfunction (Vertigo disorder) in wistar rats".

Animal Welfare:

Study is approved by the Institutional Animal ethics committee and committee for the purpose of control and supervision of experiments on animals (CPCSEA).

Test System Details:

- Test Species: Rat
- Strain: Albino Wistar
- Sex: Male/Female
- Age: 6-8 Weeks
- Body Weight: 180-200 g
- Source: In house breed
- Total No. of Animals: 42 Animals (7 groups of 6 animals each)
- Feed: Normal chow diet (Purina lab diet 5L79 Rat and Mouse 18%) (PMI Nutrition International)

Environmental Conditions:

The temperature of the experimental room was maintained at 22° C.±3° C. and the relative humidity between 30-70% and the photoperiod was about 12 hours light and 12 hours dark cycles, experimental room was cleaned daily with disinfectant.

Drinking water: Rat was provided with ad libitum drinking water passed through water filter system in autoclaved poly propylene bottles.

Housing Conditions:

Three rats/cage were housed in autoclaved polypropylene cages using autoclaved paddy husk as the bedding material. Each cage was fitted with top grill having provision for keeping rodent feed and water bottle.

Vehicle details: 0.5% of Carboxy Methyl Cellulose sodium was used as a vehicle for test formulation.

Group, Designation and Dose Levels:

TABLE 1

Animal grouping and treatment details

| Groups | Group Description | Human Dose | No. of animals |
|---|---|---|---|
| Group 1 | Normal control | Vehicle | 6 |
| Group 2 | Disease Control | Sodium Arsanilate | 6 |
| Group 3 | Reference standard | Vertin-8 mg | 6 |
| Group 4 | Test - NADLL | Proposed dose-500 mg | 6 |
| Group 5 | Test - UMP | Proposed dose- 3 mg | 6 |
| Group 6 | Test - NADLL:UMP | [Low ratio 500 mg:3 mg] | 6 |
| Group 7 | Test - NADLL:UMP | [High ratio 100 mg:50 mg] | 6 |

Study Procedure:

Induction of Vestibular Dysfunction—

Vestibular dysfunction was induced in rats by intratympanic injection of sodium arsanilate an ototoxic compound. Sodium arsanilate is an arsenic derivative and intratympanic injection result was vestibular nerve degeneration in brain stem with concomitant loss of labyrinthine righting and reduced postural support with exaggerated head dorsiflexion.

Behavioral studies were conducted to examine the learning and memory ability by using following tests Air reflecting index Contact righting reflex Open field test Administration and Procedure:

All the animals were acclimatized for at least 5 days under controlled environmental condition. Total 42 animals were divided into seven groups consisting of 6 animals per group. Normal control (G1) group receiving vehicle, disease control (G2) group receiving sodium arsanilate injection only, standard group (G3) receiving reference standard (vertin) and treatment groups G4, G5, G6 & G7 were treated with the test substances. All the groups (except normal control group) were induced with sodium arsanilate via intratymphanic injection. All the treatment groups were administered daily for 7 consecutive days.

The following behavioral test was conducted at the end of the treatment,

Air reflecting index

Contact righting reflex

Open field test

Behavioral Evaluation Tests

Air Reflecting Index

A sponge was spread on a flat surface and the animals were placed in a supine position in the air 50 cm away above the sponge, following which the animal was dropped horizontally.

Four-legged smooth landing on the ground was considered as positive (normal animal), whereas the body or other regions landing first was considered vestibular dysfunction animals. The positive landing rate (%) of each rat in each group was recorded.

Contact Righting Reflex

The rats were placed in a syringe core tube in a supine position, following which the recovery time for position correction to be recorded. Normal rats turned over their body position in a few seconds. However, rats with vestibular dysfunction exhibited difficultly in identifying the inverted position, and thus failed to turn over their body position with prolonged time.

Open Field Test

Apparatus:

The open-field was circular, with a diameter of 90 cm, and enclosed by a wall 30 cm high. The floor and wall of the open-field was black and the floor was divided into 25 equal area sections by thin white lines. The floor was covered with a transparent plastic coating. The open-field apparatus was located inside a large wooden frame which surrounded on all sides by black curtains. The field was illuminated by two 60-W fluorescent lights located 100 cm above the floor.

Test Procedure:

At the start of each session the rats were placed in one of the peripheral sections of the open-field and the animal's behavior was monitored by an observer for 10 consecutive minutes. The following variables were recorded for each 2-minute segment of the test session: 1) ambulation—the number of open-field sections entered by the subject; 2) rearing responses—the number of times the animal raised both forefeet off the floor and extended its body; 3) defecation—the number of fecal boli deposited in the open-field; 4) grooming—the number of grooming bouts exhibited by the rat. At the end of each session the rat was returned to its home cage and the floor of the open-field was cleaned and sponged over with a weak vinegar solution to remove any residual odors.

Study Observations

Mortality and Morbidity

The cage-side examinations were conducted to detect moribund or dead animals and abnormal behavior and/or appearance in animals, at least twice daily throughout the study.

Body Weight

Individual body weights were recorded at receipt, on the day of randomization, on the first day of treatment before dosing and weekly once thereafter throughout the treatment period. The body weight changes for all the animals were calculated and reported along with the body weight data.

Feed Consumption

The feed consumption was calculated and reported on a daily basis throughout the study period.

Statistical Analysis

All data including body weight, feed consumption, was analyzed statistically using Graph-Pad Prism Software, version 5.01. All values will be expressed as Mean±SD. The significant difference between the treatment and control group was estimated using one-way ANOVA with Dunnett's test. All results of the statistical analysis were summarized in separate tables.

Results:

TABLE 2

| Effect of test substances on Rat Body Weight Body Weight (gm) | | | |
|---|---|---|---|
| Group | Treatment | Initial | End of the treatment |
| Group 1 | Normal control | 189.68 | 191.13 |
| Group 2 | Disease Control | 185.92 | 186.98 |
| Group 3 | Reference standard | 186.83 | 188.10 |
| Group 4 | Test - NADLL | 189.15 | 190.77 |
| Group 5 | Test - UMP | 189.02 | 190.08 |
| Group 6 | Test - NADLL:UMP [Low ratio] | 190.43 | 192.02 |
| Group 7 | Test - NADLL:UMP [High ratio] | 186.50 | 188.22 |

TABLE 3

| Effect of test substances on Rat Feed Consumption Feed Consumption (gm) | | | |
|---|---|---|---|
| Group | | 0 day | $7^{th}$ day |
| Group 1 | Normal control | 15.83 | 16.50 |
| Group 2 | Disease Control | 14.50 | 15.17 |
| Group 3 | Reference standard | 15.33 | 16.00 |
| Group 4 | Test - L-TAMS | 16.00 | 16.67 |
| Group 5 | Test - HT | 15.50 | 16.67 |
| Group 6 | Test - L-TAMS:HT | 15.33 | 16.50 |
| Group 7 | Test - L-TAMS:HT | 16.00 | 17.00 |

TABLE 4

| Air Righting Reflex (% of Rats that successfully righted themselves within 5 s) | | | | | | | |
|---|---|---|---|---|---|---|---|
| | Animals | | | | | | |
| Groups | 1 | 2 | 3 | 4 | 5 | 6 | Average |
| | Successful out of 5 | | | | | | |
| Group 1 | 5 | 4 | 5 | 4 | 4 | 5 | |
| % | 100 | 80 | 100 | 80 | 80 | 100 | 90.00 |
| Group 2 | 1 | 2 | 0 | 1 | 2 | 1 | |
| % | 20 | 40 | 0 | 20 | 40 | 20 | 23.33 |
| Group 3 | 2 | 3 | 2 | 3 | 2 | 3 | |
| % | 40 | 60 | 40 | 60 | 40 | 60 | 50.00 |
| Group 4 | 2 | 3 | 2 | 2 | 3 | 2 | |
| % | 40 | 60 | 40 | 40 | 60 | 40 | 46.67 |
| Group 5 | 2 | 2 | 1 | 2 | 1 | 2 | |
| % | 40 | 40 | 20 | 40 | 20 | 40 | 33.33 |
| Group 6 | 4 | 5 | 4 | 3 | 5 | 5 | |
| % | 80 | 100 | 80 | 60 | 100 | 100 | 86.67 |
| Group 7 | 3 | 4 | 5 | 4 | 5 | 4 | |
| % | 60 | 80 | 100 | 80 | 100 | 80 | 83.33 |

TABLE 5

| Contact righting reflex (time (sec)) | | | | | | | |
|---|---|---|---|---|---|---|---|
| | Animals | | | | | | |
| Groups | 1 | 2 | 3 | 4 | 5 | 6 | Average |
| Group 1 | 3 | 4 | 3 | 5 | 2 | 4 | 3.50 |
| Group 2 | 42 | 37 | 32 | 45 | 41 | 47 | 40.67 |
| Group 3 | 21 | 26 | 28 | 23 | 27 | 26 | 25.17 |
| Group 4 | 27 | 26 | 25 | 28 | 27 | 28 | 26.83 |
| Group 5 | 30 | 29 | 28 | 27 | 30 | 26 | 28.33 |
| Group 6 | 11 | 8 | 10 | 11 | 9 | 10 | 9.83 |
| Group 7 | 10 | 10 | 9 | 9 | 10 | 12 | 10.00 |

TABLE 6

| Ambulation Score [the number of open-field sections entered by the rat] | | | | | | | |
|---|---|---|---|---|---|---|---|
| | Animals | | | | | | |
| Groups | 1 | 2 | 3 | 4 | 5 | 6 | Average |
| Group 1 | 90 | 100 | 87 | 110 | 94 | 95 | 96.00 |
| Group 2 | 250 | 240 | 260 | 245 | 255 | 260 | 251.67 |
| Group 3 | 200 | 210 | 215 | 230 | 220 | 225 | 216.67 |
| Group 4 | 210 | 200 | 220 | 220 | 210 | 220 | 213.33 |
| Group 5 | 200 | 180 | 190 | 160 | 200 | 190 | 186.67 |
| Group 6 | 90 | 100 | 100 | 110 | 100 | 90 | 98.33 |
| Group 7 | 90 | 110 | 100 | 95 | 90 | 100 | 97.50 |

TABLE 7

| Rearing Responses [the number of times the animal raised both forefeet off the floor and extended its body] | | | | | | | |
|---|---|---|---|---|---|---|---|
| | Animals | | | | | | |
| Groups | 1 | 2 | 3 | 4 | 5 | 6 | Average |
| Group 1 | 10 | 11 | 12 | 12 | 10 | 9 | 10.67 |
| Group 2 | 2 | 3 | 2 | 2 | 3 | 2 | 2.33 |
| Group 3 | 5 | 4 | 6 | 4 | 5 | 4 | 4.67 |
| Group 4 | 4 | 3 | 5 | 4 | 6 | 4 | 4.33 |
| Group 5 | 3 | 4 | 3 | 4 | 3 | 4 | 3.50 |
| Group 6 | 7 | 8 | 10 | 9 | 9 | 8 | 8.50 |
| Group 7 | 8 | 9 | 7 | 9 | 8 | 9 | 8.33 |

TABLE 8

| Defecation [the number of fecal boli deposited in the open-field] | | | | | | | |
|---|---|---|---|---|---|---|---|
| | Animals | | | | | | |
| Groups | 1 | 2 | 3 | 4 | 5 | 6 | Average |
| Group 1 | 1 | 2 | 2 | 1 | 3 | 2 | 1.83 |
| Group 2 | 4 | 5 | 4 | 5 | 4 | 4 | 4.33 |
| Group 3 | 3 | 4 | 2 | 3 | 4 | 3 | 3.17 |
| Group 4 | 2 | 3 | 4 | 2 | 3 | 4 | 3.00 |
| Group 5 | 4 | 2 | 3 | 4 | 3 | 4 | 3.33 |
| Group 6 | 2 | 1 | 1 | 1 | 2 | 2 | 1.50 |
| Group 7 | 2 | 2 | 1 | 2 | 1 | 2 | 1.67 |

TABLE 9

| Grooming [the number of grooming bouts exhibited by the rat] | | | | | | | |
|---|---|---|---|---|---|---|---|
| | Animals | | | | | | |
| Groups | 1 | 2 | 3 | 4 | 5 | 6 | Average |
| Group 1 | 2 | 3 | 2 | 1 | 2 | 1 | 1.83 |
| Group 2 | 7 | 9 | 8 | 6 | 8 | 9 | 7.83 |
| Group 3 | 4 | 3 | 3 | 5 | 6 | 5 | 4.33 |
| Group 4 | 3 | 4 | 3 | 3 | 4 | 2 | 3.17 |
| Group 5 | 2 | 4 | 3 | 3 | 4 | 4 | 3.33 |
| Group 6 | 2 | 1 | 1 | 2 | 1 | 1 | 1.33 |
| Group 7 | 1 | 2 | 2 | 1 | 2 | 1 | 1.50 |

Figure 2:
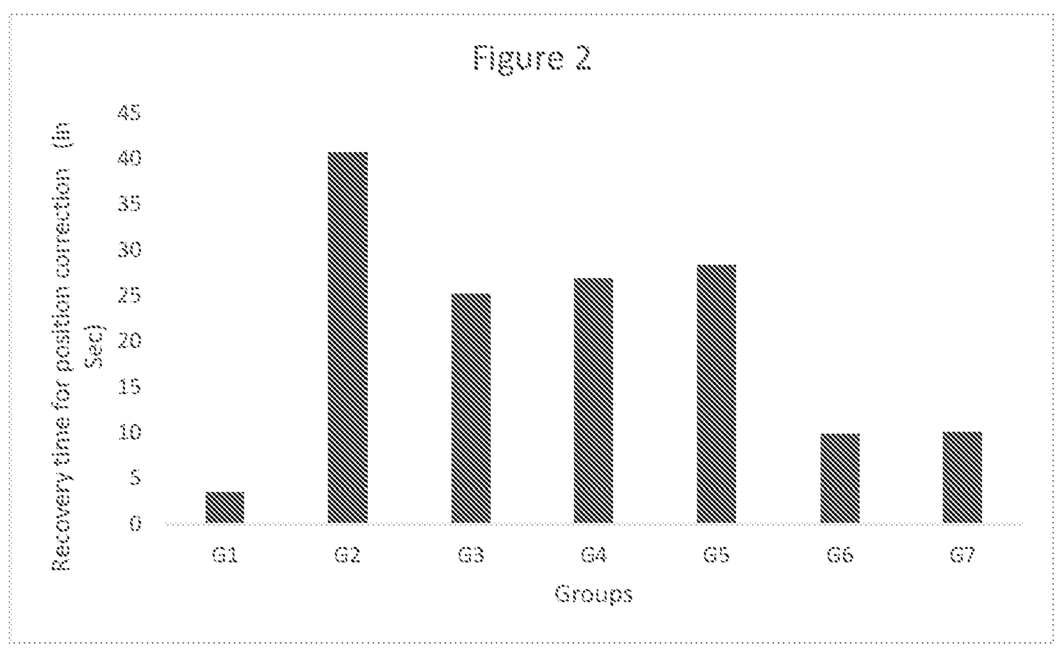
FIG. 2 illustrates contact righting reflex (recovery time for position correction) G1: Normal Control, G2: Disease Control, G3: Reference Standard, G4: NADLL enriched with L-leucine, G5: UMP, G6: NADLL+UMP (Low Ratio), G7: NADLL+UMP (High Ratio).
Figure 3:
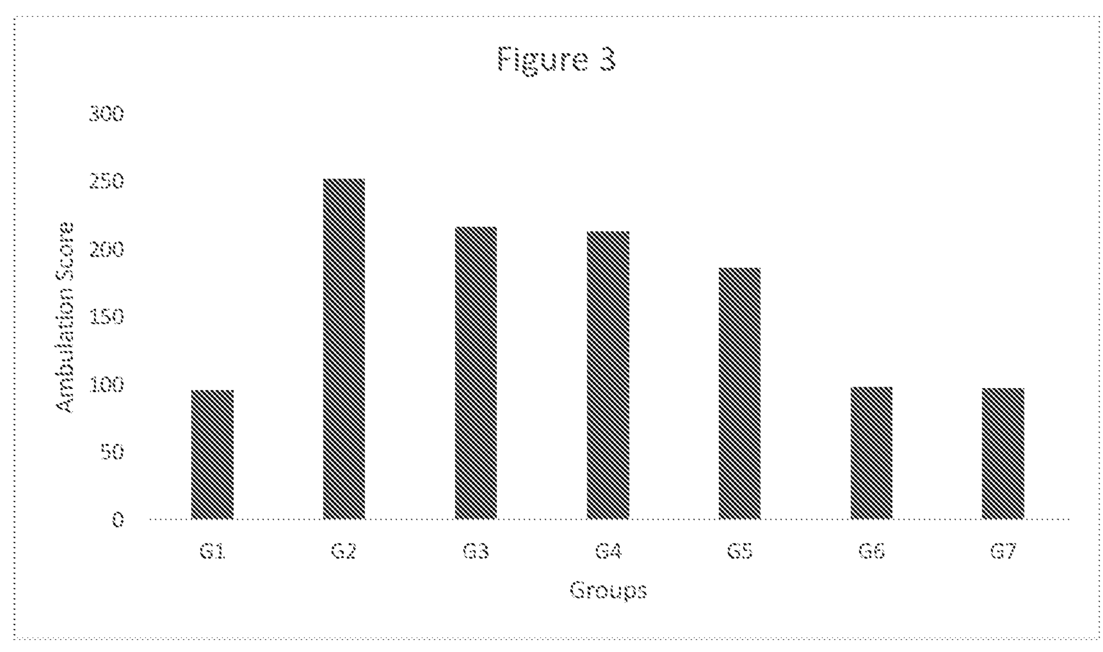
FIG. 3 illustrates ambulation score in open field test G1: Normal Control, G2: Disease Control, G3: Reference Standard, G4: NADLL enriched with L-leucine, G5: UMP, G6: NADLL+UMP (Low Ratio), G7: NADLL+UMP (High Ratio).
Figure 4:
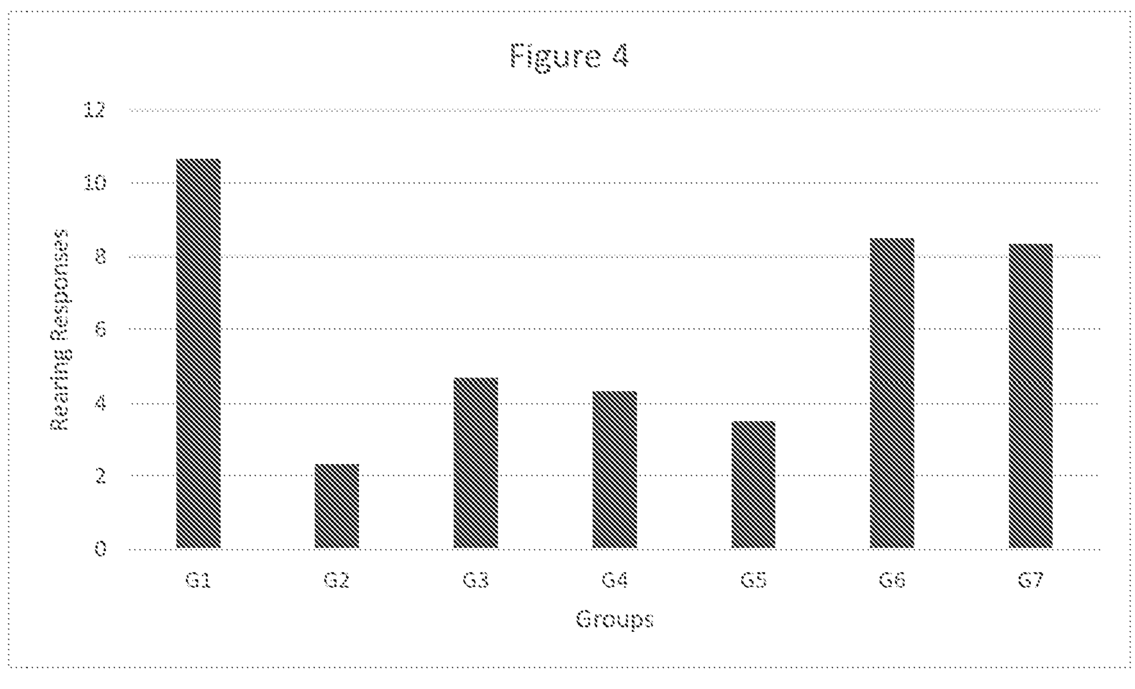
FIG. 4 illustrates rearing responses in open field G1: Normal Control, G2: Disease Control, G3: Reference Standard, G4: NADLL enriched with L-leucine, G5: UMP, G6: NADLL+UMP (Low Ratio), G7: NADLL+UMP (High Ratio).
Figure 5:
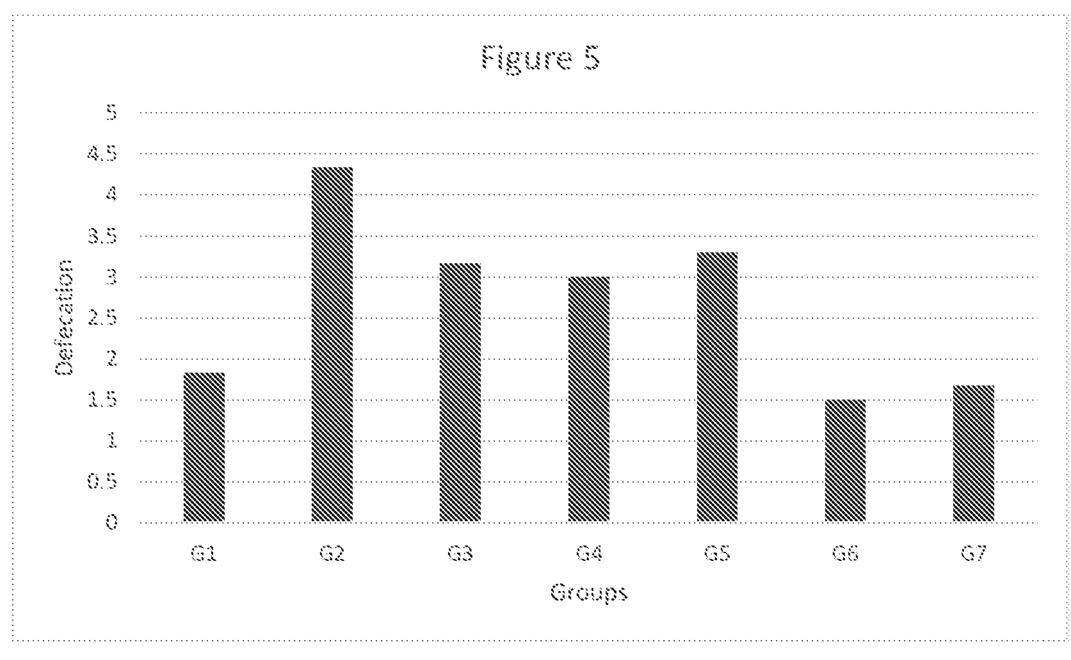
FIG. 5 illustrates defecation count (open filed test) G1: Normal Control, G2: Disease Control, G3: Reference Standard, G4: NADLL enriched with L-leucine, G5: UMP, G6: NADLL+UMP (Low Ratio), G7: NADLL+UMP (High Ratio).
Figure 6:
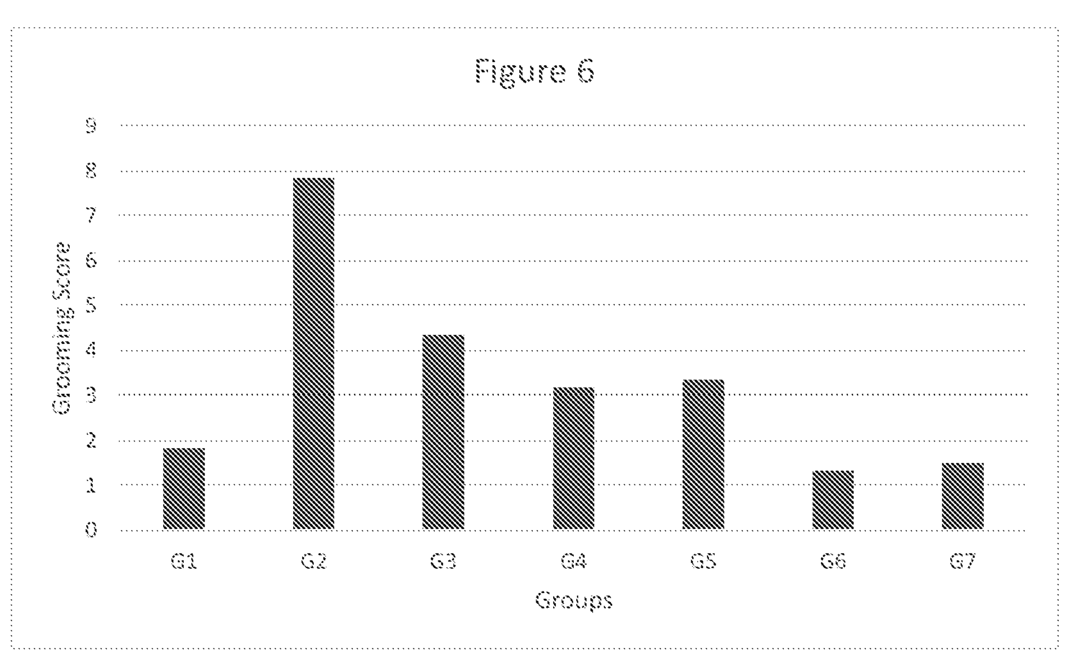
FIG. 6 illustrates grooming time (open filed test) G1: Normal Control, G2: Disease Control, G3: Reference Standard, G4: NADLL enriched with L-leucine, G5: UMP, G6: NADLL+UMP (Low Ratio), G7: NADLL+UMP (High Ratio).

The present investigation demonstrated the neuroprotective activity of test substances against vestibular dysfunction (Vertigo disorder) in wistar rats. It did not show any significant changes on body weight in all the groups observed when compared with disease control group (G2) (Table 2). Table 3 represents the Feed intake of rat was not showing any significant changes observed in all the groups when compared with disease control group (G2). Table 4 and FIG. 1 represent air righting reflex (% of Rats that successfully righted themselves within 5 seconds) which showed significant increase in the G6 and G7 treated group when compared with Control group (G2). Table 5 and FIG. 2 represent contact righting reflex (recovery time for position correction) which showed significant decrease in G6 and G7 treated group when compared with Control group (G2). Table 6 and FIG. 3 represent ambulation score in open field test which showed significant decrease in G6 and G7 treated group when compared with Control group (G2). Table 7 and FIG. 4 represent rearing responses in open field test which showed quick response in G6 and G7 treated group when compared with Control group (G2). Table 8 and FIG. 5 represent significant decrease in defecation in G6 and G7 treated group when compared with Control group (G2). Table 9 and FIG. 6 represent significant improvement in grooming in G6 and G7 treated group when compared with Control group (G2).

The results showed that the present test substances in combination improve vestibular dysfunction effectively. In the air righting reflex the combination provides up to 86.67% result which is very close to the normal control i.e., 90% when compared with individual test substances G4 and G5 i.e., 46.67% and 33.33% respectively. In the second test, contact righting reflex, the combination (G6 & G7) provides improvement up to 75% (wrt. the Disease Control) in comparison with the individual ingredients G4 and G5 which is up to 34% and 30% respectively as well as in comparison with the standard G3 which give results around 38%.

The combination also provides better results in the open field test when compared with individual ingredients as well as the standard (reference), which are disclosed as follows in Table 10.

TABLE 10

| Results | | | | |
|---|---|---|---|---|
| Groups | % Improvement in Ambulation score wrt. G2 | % Improvement in Rearing Responses wrt. G2 | % Improvement in Defecation wrt. G2 | % Improvement in Grooming wrt. G2 |
| G3 | 13.91 | 43.75 | 26.92 | 44.68 |
| G4 | 15.23 | 40.62 | 30.77 | 59.57 |
| G5 | 25.83 | 32.81 | 23.08 | 57.45 |
| G6 | 60.93 | 79.68 | 65.38 | 82.98 |
| G7 | 61.26 | 78.12 | 61.50 | 80.85 |

It is concluded that, the test substance i.e., combination of NADLL+UMP in low ratio (G6) and high ratio (G7) effectively improve vestibular dysfunction associated cognitive impairment.

We claim:

1. A synergistic composition for treating vestibular associated neurodegenerative diseases, the composition comprising: an exogenous blend of N-acetyl-DL-leucine enriched with L-leucine and uridine monophosphate, wherein the exogenous blend comprises N-acetyl-DL-leucine enriched with L-leucine and uridine monophosphate, and wherein a weight ratio of N-acetyl-DL-leucine enriched with L-leucine to uridine monophosphate is in a range of 1:0.002 to 1:0.8.

2. The synergistic composition as claimed in claim 1, wherein the N-acetyl-DL-leucine enriched with the L-leucine is present in a range of 50% to 98% by weight of the total composition.

3. The synergistic composition as claimed in claim 1, wherein the uridine monophosphate is present in a range of 0.1% to 35% by weight of the total composition.

4. The synergistic composition as claimed in claim 1, wherein the N-acetyl-DL-leucine comprises D-leucine in a range of 5% to 45% and the L-leucine in a range of 55% to 95% by weight of the total N-acetyl-DL-leucine.

5. The synergistic composition as claimed in claim 1, wherein the N-acetyl-DL-leucine enriched with the L-leucine and the uridine monophosphate are present in a white crystalline form.

6. The synergistic composition as claimed in claim 1, wherein the pharmaceutically acceptable excipients are selected from a group consisting of a diluent present in a range of 1 to 30%; a binder present in a range of 0.1 to 25%; a lubricant present in a range of 0.1 to 10.0%; a glidant present in a range of 0.1 to 5.0%; an additive present in a range of 1 to 10%; a surfactant present in a range of 0.1 to 5.0%; a stabilizer present in a range of 0.1 to 5.0%, an antioxidant present in a range of 0.1 to 5.0%; and a plasticizer present in a range of 0.1 to 5.0%, by weight of the total composition.

7. The synergistic composition as claimed in claim 1, wherein the vestibular associated neurodegenerative diseases are selected from a group consisting of dizziness, imbalance, vertigo, tinnitus, hearing loss, brain fog, vision impairment, cognitive changes, Alzheimer's disease, progressive supranuclear palsy (PSP), frontotemporal dementia (FTD), motor neurone disease (MND), multiple system atrophy (MSA), and Parkinson's disease (PD).

* * * * *